United States Patent [19]

Kadar

[11] Patent Number: 5,565,768
[45] Date of Patent: Oct. 15, 1996

[54] APPARATUS FOR DETECTING METALLIC DEBRIS IN DIELECTRIC FLUID HAVING AN INDIRECTLY HEATED THERMISTOR FOR BALANCING A BRIDGE NETWORK

[75] Inventor: Miklos P. Kadar, Beachwood, N.J.

[73] Assignee: Smiths, Industries Aerospace & Defense Systems, Inc., Grand Rapids, Mich.

[21] Appl. No.: 337,562

[22] Filed: Nov. 10, 1994

[51] Int. Cl.$^6$ ............ G01N 27/74; G01N 33/28; G01R 33/12; H03H 1/00
[52] U.S. Cl. ............ 324/204; 324/234; 324/236; 324/651; 340/631; 323/369
[58] Field of Search ............ 324/204, 234–238, 324/225, 71.1, 207.15, 207.16, 654, 233, 649–651, 445, 442, 698; 340/631; 73/10, 861.08, 861.11, 61.42, 204.15, 204.16; 333/219.1, 219.2; 338/22 R, 23; 323/369

[56] References Cited

U.S. PATENT DOCUMENTS

| 4,173,975 | 11/1979 | Delong et al. | 324/204 |
| 4,926,120 | 5/1990 | Veronesi et al. | 340/631 |
| 5,041,856 | 8/1991 | Veronesi et al. | 324/236 |
| 5,089,781 | 2/1992 | Arichika et al. | 324/204 X |
| 5,269,170 | 12/1993 | Meyer | 324/204 |

FOREIGN PATENT DOCUMENTS

| 210468 | 7/1965 | U.S.S.R. | 324/204 |
| 216118 | 4/1967 | U.S.S.R. | 324/204 |
| 873912 | 6/1958 | United Kingdom | 324/204 |

*Primary Examiner*—Sandra L. O'Shea
*Assistant Examiner*—Jay M. Patidar
*Attorney, Agent, or Firm*—Varnum, Riddering, Schmidt & Howlett

[57] ABSTRACT

In an inductive debris monitor (IDM) an inductive probe is disposed at a fluid flow passageway to be monitored, and an RF bridge containing a variable resistance network is used to detect changes in the impedance of the probe due to the passage of metallic debris. An indirectly heated thermistor is utilized in the resistance network for balancing the bridge. Thus the operating temperature range is significantly extended without compromising reliability or experiencing degradation.

21 Claims, 1 Drawing Sheet

APPARATUS FOR DETECTING METALLIC DEBRIS IN DIELECTRIC FLUID HAVING AN INDIRECTLY HEATED THERMISTOR FOR BALANCING A BRIDGE NETWORK

BACKGROUND OF THE INVENTION

1. Field of the Invention

The present invention relates to sensors for the detection of metallic debris in dielectric fluids using high frequency electromagnetic fields and more particularly to an inductive debris monitor (IDM) having a sensor system with an extended operating temperature range and improved reliability.

2. Description of the Prior Art

Sensors are known for detecting metallic debris in fluid flow passageways such as in engine and transmission lubricating systems where the presence of metal particles in the dielectric fluid lines can be an indication of the impending failure of the system. Sensing systems of this type are disclosed in U.S. Pat. Nos. 4,926,120 and 5,041,856, issued to W. A. Veronesi et al and assigned to United Technologies Corp., and in U.S. Pat. No. 5,357,197 of Lev Sorkin and co-pending U.S. application Ser. No. 08/143,846 of Gerald Pulice, both assigned to the same assignee as the present application. It is common in such systems, as in the system disclosed, for example, in U.S. Pat. No. 4,926,120, to use a radio frequency (RF) bridge with the sensor to detect changes in impedance in the fluid line being monitored. Under normal operating conditions the RF bridge is automatically balanced with a voltage controlled resistor (VCR) that is implemented by means of a junction field effect silicon transistor. In particular, as shown in FIG. 3 of the exemplary patent, the RF bridge consists of a TRANSFORMER 19, 20, 21, a TANK CIRCUIT 12, 16, 18 and a VOLTAGE CONTROLLED RESISTOR 34. Among the limitations of this arrangement are the maximum operating junction temperature and the limited range of resistance as a function of the voltage control. For the RF bridge to operate over the extended temperature environment required for practical metallic debris detection, the silicon VCR poses a performance problem. Assuming a silicon-carbide based technology were substituted for the junction field effect transistor, such an arrangement would have a maximum permissible operating junction temperature of about 350° C., in contrast to the maximum temperature of about 175° C. for the silicon based device. However, the limited range of resistance control would still pose a technical limit.

It is therefore a problem in the art to achieve a desirable range of resistance control in IDM devices over an extended operating temperature range.

It is accordingly an object of the present invention to provide an improved metallic particle sensor and bridge arrangement that overcomes the operating temperature range and reliability limitations of the prior art IDM sensor systems.

It is another object of the invention to provide an improved means for balancing the RF bridge in IDM devices that enables their operation over a very wide range of temperatures without reliability problems or degradation.

It is also an object of the invention to provide a bridge arrangement that will provide improved operation with IDM devices wherein the resonance impedance decreases with increasing temperature.

It is a further object of the invention to provide a sensor and bridge arrangement with minimum interactions between the bridge circuit and the surrounding environment.

SUMMARY OF THE INVENTION

The present invention involves a sensing system for detecting and categorizing metallic debris present in dielectric fluid flow and is particularly directed to the implementation of an IDM device having an extended temperature range of operation. Typically IDM devices currently use RF bridges for detecting impedance changes resulting from the sensing of metallic debris by an inductive probe disposed at the fluid flow passage being monitored. The RF bridge is balanced by a voltage controlled resistor connected in the bridge circuit. In accordance with the invention, an indirectly heated thermistor is substituted for the junction field effect silicon transistor conventionally used as the voltage controlled resistor. Such a thermistor can operate in the resulting bridge circuit arrangement over a very wide range of temperatures, including beyond 350° C., without compromising reliability or experiencing degradation. Also, due to the electrically isolated nature of indirectly heated thermistors, interactions between the bridge circuit and the surrounding environment are reduced thus improving accuracy and performance.

BRIEF DESCRIPTION OF THE DRAWINGS

The FIGURE is a schematic diagram of a sensor and bridge circuit in accordance with the invention showing the indirectly heated thermistor and its associated circuitry.

DETAILED DESCRIPTION OF THE PREFERRED EMBODIMENT

Figure 1:
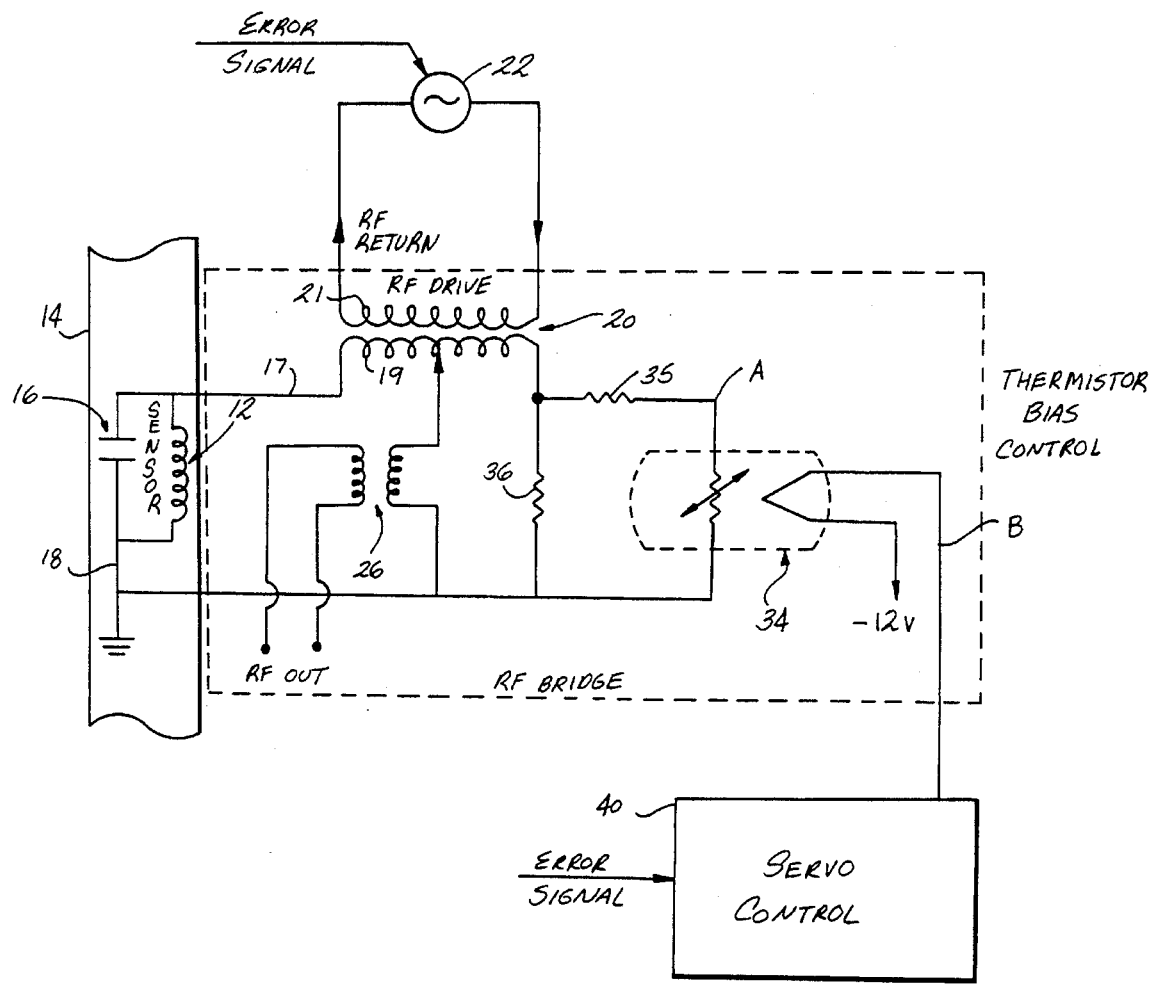

As seen in the drawing FIGURE the sensor and bridge circuit of the invention are composed firstly of a probe or sensing device in the form of a tank circuit, i.e., inductance coil(s) 12 and capacitor(s) 16, which is disposed at a fluid flow passageway 14 to detect changes in the electromagnetic field therein due to the passing of metallic debris. One lead 18 from the tank circuit 12, 16, is an isolated ground and the other lead 17 is coupled to a variable resistance bridge by being connected to one end of a center-tapped transformer winding 19 of a driving transformer 20. Transformer 20 has an opposite winding 21 supplied with a high frequency, typically radio frequency (RF), alternating electric current from a voltage controlled oscillator 22 so as to operate as an RF driver for the tank and bridge circuits. The tank circuit 12, 16, is driven at the resonance frequency to create an electromagnetic field in the flow passageway 14, which field is disturbed by passing metallic debris resulting in changes in the impedance characteristics of the circuit. Such changes cause imbalance in the bridge circuit resulting in current flow through coupling transformer 26. The imbalance due to impedance changes of the tank circuit 12, 16 is tied by lead 17 to drive transformer 20 and is countered by a variable resistance network, containing an indirectly heated thermistor 34, such as a modified 42A2 thermistor sold by Victory Engineering, disposed in series with a resistor 35 and in parallel with a resistor 36. This network is located between winding 19 and ground, and forms the balancing part of a variable resistance RF bridge.

In operation, the alternating electromagnetic field generated by winding 21 induces an alternating electric current in winding 19, which current is tuned to drive the tank circuit at a frequency at or close to resonance when the flow passageway is comparatively free of metallic debris. The RF pickup 26 outputs an alternating current signal derived from the current in coil 19 and thus indicative of the current which flows into and out of the tank circuit 12, 16, which current, in turn, reflects changes in the field in the flow passageway 14. A comparison of the driving and the pick-up current is made to determine respective in-phase and quadrature errors. These determinations are used to provide respective resistive (in-phase) and reactive (quadrature) error signals from which the character and size of any metallic particles present in the passageway can be evaluated by suitable evaluating circuitry. The reactive error signal is fed through an amplifier to the voltage controlled oscillator 22 that drives transformer 20 to change its operating frequency in accordance with the magnitude of this error signal.

The resistive error signal is also fed through an amplifier to the indirectly heated thermistor 34 which is interposed with resistors 35 and 36 between winding 19 and ground. The resistance of the thermistor 34 will vary, in dependence on the magnitude of the amplified resistive error signal, toward balancing the bridge.

The thermistor unit is essentially electrically isolated having an interconnect point A to the winding 19 and an interconnect point B to a servo control circuit 40 and associated electronics.

The use of an indirectly heated thermistor is of advantage in this application since its material enables it to operate through a very wide range of temperatures, even beyond 350° C., without affecting reliability or degradation. Further, the invention can be readily incorporated in existing IDM devices with advantage. For example, the device disclosed in above-cited U.S. Pat. No. 5,041,856 has the characteristic of decreasing resonance impedance with increasing temperature, which is advantageous when using a negative temperature coefficient thermistor, so that with a single indirectly heated thermistor a wide temperature range control can easily be accomplished in this application.

Due to the electrically isolated nature of the indirectly heated thermistor, interactions between the bridge circuit and the environment are completely eliminated due to electrical isolation of the thermistor bead from its heater element.

While the present invention has been described in terms of specific embodiments and combinations, it will be appreciated that the invention is not limited to the particular examples presented herein, and that the scope of the protection is defined in the attached claims.

I claim:

1. Apparatus for detecting metallic debris in a flow passageway conducting dielectric fluid containing metallic debris, comprising:
   sensing means, disposed at said passageway, for sensing the passage of metallic material and producing an electric signal indicative thereof;
   impedance network means, coupled to said sensing means, for receiving said indicative electric signal and producing an output in response thereto that indicates the detection of metallic material in said flow, said network means comprising:
   indirectly heated thermistor means for electrically balancing said network means in response to said output.

2. Apparatus as in claim 1, wherein said network means further comprises a resistance in series with and a resistance in parallel with said indirectly heated thermistor means.

3. Apparatus as in claim 1, wherein said thermistor means comprises a negative temperature coefficient thermistor.

4. Apparatus as in claim 1, wherein said sensing means comprises a resonant circuit disposed at said passageway to sense changes in the fluid flow therein by changes in the impedance of said resonant circuit.

5. Apparatus as in claim 1, wherein said output comprises a signal indicative of a resistive (in-phase) error and a signal indicative of a reactive (quadrature) error and said indirectly heated thermistor means comprises a resistive bead element and a separate heating element and the heating of said heating element is responsive to said signal indicative of a resistive (in-phase) error to control the resistance of said resistive bead element.

6. Apparatus as in claim 5, wherein said heating element comprises an electrically heated filament and further comprising sealed and evacuated means for containing said heated filament and bead therein protected from the ambient environment.

7. Apparatus as in claim 5, further comprising oscillator means for providing a driving current to said sensing means and said network means, and means, responsive to said reactive (quadrature) error signal, for changing said driving current in accordance with said reactive (quadrature) error.

8. Apparatus having an extended operating temperature range and improved reliability for sensing metallic debris in a flow passageway conducting dielectric fluid in which metallic debris may be contained, comprising:
   detector means, disposed at said passageway and having an impedance, for detecting changes in said fluid flow by changes in said impedance, and responsive to the passing of metallic debris in the flow in said passageway, for producing signals indicative of changes of impedance caused by changes in said flow;
   bridge means, having a predetermined impedance and coupled to said detector means, said bridge means comprising:
   means for sensing an indicative signal and producing an error signal in accordance with the change of impedance represented thereby; and
   indirectly heated thermistor means having a resistive element forming a portion of said predetermined impedance and a heating element responsive to said error signal for changing the resistance of said resistive element in accordance with said error signal and thereby said predetermined impedance of said bridge means to balance said ridge means.

9. Apparatus as in claim 8, wherein said thermistor means comprises a negative temperature coefficient thermistor.

10. Apparatus as in claim 8, further comprising oscillator means for providing a driving current to said detector means and said bridge means, and means, responsive to said error signal, for changing said driving current in accordance with said error signal.

11. Apparatus as in claim 8, wherein said detector means comprises a resonant circuit disposed at said passageway to sense changes in the fluid flow therein by changes in the impedance of said resonant circuit.

12. Apparatus as in claim 8, wherein said bridge means further comprises a resistance in series with and a resistance in parallel with said indirectly heated thermistor means.

13. A method for detecting metallic material in a flow passageway conducting dielectric fluid flow in which metallic particles may occur, comprising the steps of:
   sensing a change of magnetic field in said passageway due to the passage of metallic particles in said dielectric fluid flow by an electromagnetic sensing device electrically connected to balancing bridge network having a variable impedance, and producing an electric signal indicative of change in impedance in said electromagnetic sensing device due to said change in magnetic field;

inputting said indicative electric signal to said balancing bridge network and producing an output, in response to said input, indicating the detection of metallic particles in said flow; and controlling an indirectly heated thermistor in said bridge network for electrically changing the variable impedance of said bridge network in accordance with said electrical signal.

14. A method as in claim 13, wherein said bridge network further comprises a resistance in series with and a resistance in parallel with said indirectly heated thermistor.

15. A method as in claim 13, wherein said indirectly heated thermistor is a negative temperature coefficient thermistor.

16. A method as in claim 13, wherein said output comprises a signal indicative of a resistive (in-phase) error and a signal indicative of a reactive (quadrature) error and said indirectly heated thermistor is responsive to said signal indicative of a resistive (in-phase) error in electrically balancing the impedance of said bridge network.

17. A method as in claim 16, wherein said indirectly heated thermistor comprises a resistive bead and a separate heating element and the heating of said heating element is responsive to said signal indicative of a resistive (in-phase) error, and further comprising the step of sealing said resistive bead and said heating element together from said ambient environment.

18. A method as in claim 16, wherein said sensing step is carried out by a resonant circuit and further comprising the steps of providing a driving current to said resonant circuit and said bridge network, and changing said driving current in accordance with said error signal.

19. A method as in claim 13, wherein said sensing step comprises disposing a resonant circuit at said passageway to sense the passage of metallic debris by a change of impedance in said circuit and producing an electric signal indicative of said change of impedance.

20. A method as in claim 19, wherein said inputting step comprises coupling a variable impedance balancing bridge network to said resonant circuit for receiving said indicative electric signal and producing an output in response thereto comprising a signal indicative of a resistive (in-phase) error and a signal indicative of a reactive (quadrature) error caused by said change of impedance; and wherein said indirectly heated thermistor has a resistive element forming a portion of said variable impedance network and a heating element responsive to said signal indicative of the resistive (in-phase) error, to cause heat from said heating element to change the resistance of said resistive element in accordance with said resistive (in-phase) error and thereby change the variable impedance of said network to electrically balance said network in response to said output.

21. Apparatus for detecting metallic material in a flow passageway conducting dielectric fluid, comprising:

a sensor for sensing the passage of metallic material and producing an electrical signal indicative thereof;

a bridge circuit coupled to the sensor and responsive to impedance changes in the sensor to generate an error signal having a resistive component and a reactive component;

a voltage control oscillator providing an alternating current drive signal to the bridge circuit and responsive to the reactive component of the error signal to alter the drive signal;

an indirectly heated thermistor in the bridge circuit having a resistive element and heating element;

a control circuit connected to the heating element and responsive to the resistive component of the error signal to change the resistance of the resistive element in accordance with changes in the resistive component of the error signal.

* * * * *

UNITED STATES PATENT AND TRADEMARK OFFICE
CERTIFICATE OF CORRECTION

PATENT NO. : 5,565,768

DATED : October 15, 1996

INVENTOR(S) : Miklos P. Kadar

It is certified that error appears in the above-identified patent and that said Letters Patent is hereby corrected as shown below:

On the title page, item [54] and column 1, line 1

The title should read:
APPARATUS FOR DETECTING METALLIC DEBRIS IN DIELECTRIC FLUID.

Col. 1, line 23, after "Pulice":
insert --now U.S. Patent No. 5,485,083--.

Col. 4, claim 8, line 41:
delete "ridge" and substitute --bridge--.

Signed and Sealed this

Twenty-ninth Day of July, 1997

Attest:

BRUCE LEHMAN

*Attesting Officer*    *Commissioner of Patents and Trademarks*